US012631550B2

(12) United States Patent (10) Patent No.: US 12,631,550 B2

Takahashi et al. (45) Date of Patent: May 19, 2026

(54) DETERMINATION METHOD, MEASUREMENT DEVICE, AND MEASUREMENT SYSTEM

(71) Applicant: TOTOKUDO INSTITUTE LLC, Saitama (JP)

(72) Inventors: Hideyasu Takahashi, Saitama (JP); Keiko Takahashi, Saitama (JP); Rio Takahashi, Saitama (JP)

(73) Assignee: Totokudo Institute LLC, Saitama (JP)

( * ) Notice: Subject to any disclaimer, the term of this patent is extended or adjusted under 35 U.S.C. 154(b) by 44 days.

(21) Appl. No.: 18/554,571

(22) PCT Filed: Apr. 15, 2021

(86) PCT No.: PCT/JP2021/015530

§ 371 (c)(1),
(2) Date: Oct. 9, 2023

(87) PCT Pub. No.: WO2022/219764

PCT Pub. Date: Oct. 20, 2022

(65) Prior Publication Data

US 2024/0192128 A1 Jun. 13, 2024

(51) Int. Cl.
*G01N 21/27* (2006.01)
*G01N 33/48* (2006.01)
*G01N 33/493* (2006.01)

(52) U.S. Cl.
CPC ............. *G01N 21/27* (2013.01); *G01N 33/48* (2013.01); *G01N 33/493* (2013.01)

(58) Field of Classification Search
CPC ...... G01N 21/27; G01N 33/493; G01N 33/48; G01N 21/01; G01N 21/00; G01N 2021/0181; G16H 50/20; G16H 50/30
See application file for complete search history.

(56) References Cited

U.S. PATENT DOCUMENTS

2009/0086314 A1* 4/2009 Namba .................. G02B 21/34
359/383
2018/0313839 A1 11/2018 Sakairi et al.
(Continued)

FOREIGN PATENT DOCUMENTS

JP 2011-142184 7/2011
JP 2019118272 A * 7/2019 .............. C12M 1/34
(Continued)

OTHER PUBLICATIONS

Japanese Design Patent 1600045 (Year: 2018).*
(Continued)

*Primary Examiner* — Tarifur R Chowdhury
*Assistant Examiner* — Kaitlyn E Kidwell
(74) *Attorney, Agent, or Firm* — HSML P.C.

(57) ABSTRACT

A novel method for easily determining the behavior of a nematode includes: dropping a liquid containing a biological substance of a subject into a container in which a nematode is movably stored; measuring, as a reference amount, an amount related to light in a measurement range in the container irradiated with light before or immediately after the dropping of the liquid; measuring, as a determination amount, an amount related to light in the measurement range in the container irradiated with the light after an observation time provided for movement of the nematode elapses from the dropping of the liquid; and determining whether or not the determination amount has decreased by comparison with the reference amount.

7 Claims, 15 Drawing Sheets

(56)     References Cited

U.S. PATENT DOCUMENTS

| | | | |
|---|---|---|---|
| 2019/0079071 A1 | 3/2019 | Sakairi et al. | |
| 2019/0369084 A1* | 12/2019 | Hirotsu | G01N 33/48 |
| 2020/0087611 A1* | 3/2020 | He | C12M 1/3446 |
| 2020/0165655 A1* | 5/2020 | Hirotsu | G01N 33/4833 |

FOREIGN PATENT DOCUMENTS

| | | | | |
|---|---|---|---|---|
| JP | 2020-095654 | 6/2020 | | |
| JP | 2020095654 A * | 6/2020 | | G06Q 40/08 |
| WO | 2017/081750 | 5/2017 | | |
| WO | 2017/094066 | 6/2017 | | |
| WO | 2017/150569 | 5/2018 | | |

OTHER PUBLICATIONS

Hirotsu, "[online] Apr. 18, 2017 [retrieved on Jun. 29, 2021] Retrieved from the Internet:<URL: https://www.hitachi.co.jp/New/cnews/month/2017/04/0418.pdf>, pp. 1-3"—(non-official translation (Hitachi and Hirotsu Bio Science Agree to Joint Research for Practical Realization of Cancer Screenings Using Nematodes))—See English translation of ISR for a concise explanation.
International Search Report issued in International Application No. PCT/JP2021/015530, Jun. 25, 2021, 5 pages w/translation.

* cited by examiner

LIGHT SHIELDING PORTION

TRANSMISSIVE PORTION

C

C 2

C 1

LIGHT SHIELDING PORTION

TRANSMISSIVE PORTION

DETERMINATION METHOD, MEASUREMENT DEVICE, AND MEASUREMENT SYSTEM

TECHNICAL FIELD

The present invention relates to a determination method, a measurement device, and a measurement system.

BACKGROUND ART

In recent years, studies on cancer inspection methods using elongated filamentous organisms called nematodes have been actively conducted, and have attracted attention.

This inspection method utilizes chemotaxis or olfactory nerve response based on the olfactory sense of the nematodes. Since the nematodes have a property of liking an odor of urine of a cancer patient and disliking an odor of urine of a healthy person, it is possible to use the nematodes for identification of the presence or absence of cancer and the like by dropping urine of a subject in the vicinity of the nematodes and observing whether the nematodes exhibit the attracting behavior or the repelling behavior for urine.

In using the above method, a method for evaluating the behavior of the nematodes is important, but a method for accurately and inexpensively evaluating the behavior of the nematodes has not been established yet. As technology related to the evaluation of the behavior of the nematodes, for example, Patent Literature 1 is known.

Patent Literature 1 describes technology in which a plate on which nematodes and urine specimens are plotted is irradiated with light from below to capture an image, and quality control of the nematodes is performed on the basis of a temporal change in brightness in a predetermined range in the captured image. This is to evaluate the movement of the nematodes by evaluating the movement of a portion with a high brightness by utilizing the fact that the nematodes appear white and a medium appears black when the plate on which the nematodes are disposed on the medium is irradiated with light and photographed.

CITATION LIST

Patent Literature

Patent Literature 1: Re-publication No. 2017/150569

SUMMARY OF INVENTION

Technical Problem

However, in the method described in Patent Literature 1, complicated calculation including image processing and the like is required in the calculation of the brightness center of gravity, and there is a problem that the behavior of the nematodes cannot be evaluated unless a computer capable of such processing is used.

In view of the above situation, it is an object of the present invention to provide a novel method for easily determining the behavior of a nematode.

Solution to Problem

In order to solve the above problem, the present invention provides a determination method including: dropping a liquid containing a biological substance of a subject into a container in which a nematode is movably stored; measuring, as reference amount, an amount related to light in a measurement range in the container irradiated with light before or immediately after the dropping of the liquid; measuring, as a determination amount, an amount related to light in the measurement range in the container irradiated with the light after an observation time provided for movement of the nematode elapses from the dropping of the liquid; and determining whether or not it is considered that the determination amount has decreased by comparison with the reference amount.

According to the present invention, it is possible to determine the change in the amount related to the light in the measurement range before and after the movement of the nematode by the dropping of the liquid. Further, by comparing the reference amount and the determination amount in the same measurement range, even if there is a variation in the illumination condition for each container, the measurement conditions of the reference amount and the determination amount are matched, so that it is possible to accurately determine the change in the amount related to the light. Since the place where the nematode is present in the irradiated container becomes bright, it is possible to determine whether the nematode has exhibited the attracting behavior or the repelling behavior in response to the dropping of the liquid by determining whether or not it is considered that the determination amount has decreased with the above configuration.

In a preferred mode of the present invention, when it is considered that the determination amount has decreased, eligibility for insurance as a healthy person is given to the subject, and when it is considered that the determination amount has increased or when it is considered that there is no change in the determination amount, a notification for prompting an inspection is given.

With such a configuration, it is possible to give eligibility for insurance to the subject for which it is considered that the determination amount has decreased (the nematode has exhibited the repelling behavior), that is, it is considered that a possibility of cancer is low, and for example, it is possible to easily examine eligibility for insurance. Further, when it is considered that the determination amount has increased or when it is considered that there is no change in the determination amount, by giving a notification for prompting an inspection to the subject, an effect of contributing to early detection of cancer is expected.

In a preferred mode of the present invention, when a difference obtained by subtracting the reference amount from the determination amount or a ratio obtained by dividing the determination amount by the reference amount is less than a lower limit value, it is considered that the determination amount has increased. When the difference obtained by subtracting the reference amount from the determination amount or the ratio obtained by dividing the determination amount by the reference amount exceeds an upper limit value, it is considered that the determination amount has increased. When the difference obtained by subtracting the reference amount from the determination amount or the ratio obtained by dividing the determination amount by the reference amount is between the upper limit value and the lower limit value, it is considered that there is no change in the determination amount.

With such a configuration, it is possible to evaluate the change in the determination amount using a quantitative value on the basis of the upper limit value and the lower limit value set in advance.

In a preferred mode of the present invention, light of a specific wavelength is emitted at the time of measuring the reference amount and the determination amount, and amounts related to the light of the specific wavelength are measured as the reference amount and the determination amount, respectively.

With such a configuration, an influence of light other than the irradiation light can be reduced, and an effect of improving accuracy can be expected.

In a preferred mode of the present invention, the container includes a transmissive portion that transmits light on a side surface, and the transmissive portion is irradiated with light from the side surface of the container at the time of measuring the reference amount and the determination amount.

With such a configuration, the determination method according to the present invention can be used under various environments.

In order to solve the above problem, the present invention provides a measurement device for executing the determination method of aspects 1 to 5. The measurement device includes: a main body portion that covers the container; the illuminator that is provided inside a side surface of the main body portion and emits light from a side surface of the container; an input port that is provided in the main body portion to drop the liquid into the container; and a measurement unit that is provided on the main body portion and measures the amount related to the light from above the container.

According to the present invention, the illumination condition or the like can be brought close to a certain level by emitting light by the illuminator included in the main body portion covering the container, so that the effect of further improving the accuracy can be expected. Further, by providing the input port, since the liquid can be dropped in a state where the main body portion covers the container, it is not necessary to move the container or the measurement device when the liquid is dropped, the reference amount and the determination amount can be measured under a certain condition before and after the dropping, and the accuracy is improved.

In a preferred mode of the present invention, the main body portion includes the input port at a position higher than a height of the container.

With such a configuration, since the liquid can be dropped from above, the liquid can be easily dropped into an accurate position even in a state where the main body portion covers the container.

In a preferred mode of the present invention, the measurement device further includes a wheel, and the measurement unit continuously measures the reference amount and the determination amount for a plurality of containers by the measurement device being moved by the wheel.

With such a configuration, it is possible to perform the determination more efficiently.

In a preferred mode of the present invention, the main body portion includes a container introduction port for taking in and out the container on a side surface in a direction substantially perpendicular to a traveling direction of the wheel.

With such a configuration, it is possible to continuously perform the determination for the plurality of containers while moving the measurement device in a certain direction by the wheel, and the determination efficiency is improved.

In order to solve the above problem, the present invention provides a measurement system including the measurement device of aspects 8 or 9 and a floor plate. The floor plate includes a container placement portion on which the container is placed, and a boundary portion that defines a boundary between an inner side and an outer side of the container placement portion, and the wheel travels outside the container placement portion.

According to the present invention, the wheel of the measurement device can move without contacting the container, and the determination can be performed efficiently and accurately. Further, for example, when the boundary portion is expressed by unevenness, it is difficult for the wheel to enter the container placement portion, and efficiency and accuracy can be further improved.

Advantageous Effects of Invention

According to the present invention, a novel method for easily determining the behavior of a nematode can be provided.

BRIEF DESCRIPTION OF DRAWINGS

FIG. 14 is a perspective view illustrating a use example of the petri dish, the measurement device, and the floor plate in the embodiment of the present invention.

FIG. 15 is a perspective view illustrating a use example of the petri dish, the measurement device, and the floor plate in the embodiment of the present invention.

DESCRIPTION OF EMBODIMENTS

Hereinafter, a determination method according to an embodiment of the present invention will be described with reference to the drawings. Note that the following embodiments are examples of the present invention, the present invention is not limited to the following embodiments, and various configurations can be adopted.

Figure 1:
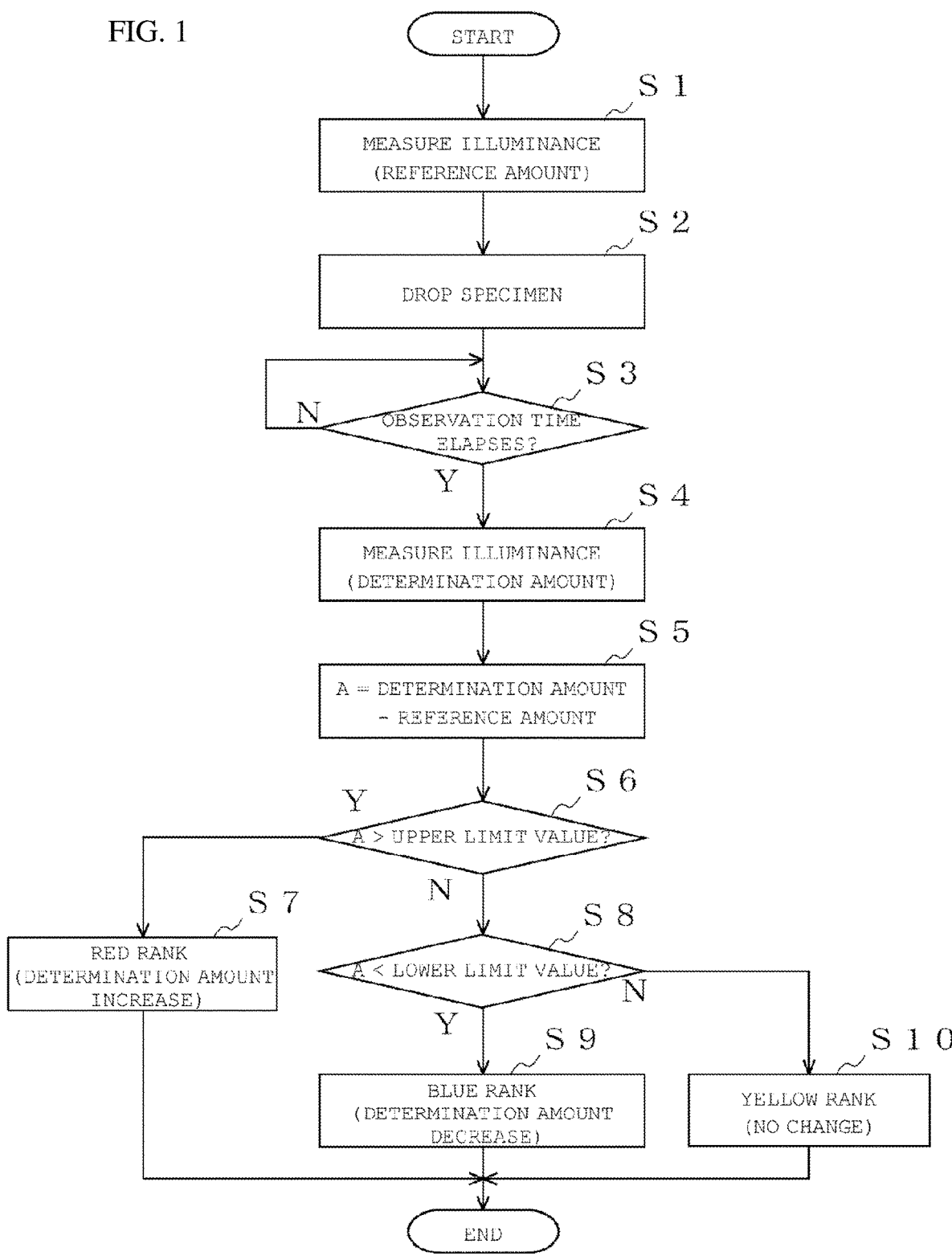
FIG. 1 is a flowchart illustrating a procedure of a determination method according to an embodiment of the present invention.

FIG. 1 is a flowchart illustrating a procedure of a determination method in the present embodiment. First, in step S1, a reference amount is measured. Here, the reference amount is an amount related to light in a measurement range in a container irradiated with light, and in the present embodiment, an illuminance with the periphery of a dropping position of a liquid containing a biological substance of a subject as a measurement range is measured as the reference amount. In addition, as the amount related to the light, it is possible to use an arbitrary index representing the intensity of light that changes due to the presence of nematodes, including a photometric quantity including a brightness or the like in a captured image of the container. The photometric quantity is a psychophysical quantity obtained by quantifying a radiation amount with the sensitivity of a human eye.

Next, in step S2, the liquid containing the biological substance of the subject is dropped into the container as a specimen. It is preferable to drop the liquid to a predetermined dropping position. In the present embodiment, a petri dish with a lid to be described later is used as the container, and the specimen is dropped near the center. Further, in the present embodiment, a liquid obtained by diluting the urine of the subject about 100 to 150 times is used as the liquid containing the biological substance of the subject.

Here, an agar medium or the like is provided on a bottom surface of the container, and the nematodes can freely move. An environment in which the nematodes can move may be provided by any other means. A sufficient number of, for example, about 100 nematodes are added to such a bottom surface in advance, and the behavior of the nematodes can be determined. As the nematode, *Caenorhabditis elegans* is suitably used, which has the advantage of having a body length of about 1 mm, having all minimum systems necessary for animals, capable of being bred at room temperature, and being relatively easy to maintain the system.

Next, in step S3, the process waits until an observation time provided for the movement of the nematode elapses. The observation time may be arbitrarily determined within a range in which the movement of the nematode can be sufficiently confirmed. For example, various conditions such as 10 seconds, 30 seconds, 60 seconds, 100 seconds, 150 seconds, 210 seconds, 280 seconds, and 360 seconds can be considered. It is preferable to specify and use the observation time at which the attracting behavior or the repelling behavior of the nematodes appears most remarkably by experiments.

When the observation time elapses after the specimen is dropped, the process proceeds to step S4, and the determination amount is measured. The determination amount is an amount related to light in the same measurement range as the reference amount, and the same index as the reference amount is used. Here, the measurement range is a range narrower than the entire container in which the nematodes can move, and is preferably a range around the specimen dropping position. In the present embodiment, the illuminance in the measurement range is used for both the reference amount and the determination amount, but as long as the reference amount and the determination amount are unified, any other index related to light that changes due to the presence of nematodes can be used as the amount related to light.

Next, in steps S5 to S10, the reference amount and the determination amount are compared to determine whether the determination amount has increased, has not changed, or has decreased. More specifically, first, in step S5, a value used for comparison between the reference amount and the determination amount is calculated. In the present embodiment, a difference obtained by subtracting the reference amount from the determination amount is calculated. Alternatively, for example, a ratio obtained by dividing the determination amount by the reference amount may be calculated and used for comparison between the reference amount and the determination amount.

Next, in step S6, the value calculated in step S5 is compared with an upper limit value. When the value calculated in step S5 exceeds the upper limit value, it is considered that the determination amount has increased (the illuminance in the measurement range has increased) after the dropping of the specimen, and a red rank is determined in step S7. In this case, it is considered that the nematodes in the container have exhibited the attracting behavior, and it can be estimated that the subject may have cancer.

When the value does not exceed the upper limit value in step S6, the process proceeds to step S8, and the value calculated in step S5 is compared with a lower limit value. When the value is less than the lower limit value, it is considered that the determination amount has decreased (the illuminance in the measurement range has decreased) after the dropping of the specimen, the process proceeds to step S9, and a blue rank is determined. In this case, it is considered that the nematodes in the container have exhibited the repelling behavior, and it can be estimated that a possibility that the subject has cancer is low.

When the value is not less than the lower limit value in step S8, it is considered that there is no change in the determination amount (there is no change in illuminance in the measurement range) before and after the dropping of the specimen, the process proceeds to step S10, and a yellow rank is determined. In this case, there is little change in identifying whether the behavior of the nematodes in the container is the attracting behavior or the repelling behavior, and it can be considered as the noise behavior.

Here, there is data that the accuracy of a cancer inspection using the reaction of the nematodes to the urine is about 85%, and there is still a problem such as difficulty in identifying the site of cancer at the present time, while the accuracy is higher than that in other methods. Therefore, it is assumed that the method according to the present invention is used not for diagnosis of cancer but for simple determination.

For example, in the case of the blue rank, since the possibility that the subject has cancer is low, eligibility for insurance as a healthy person may be given. As described above, the present invention can be used for simple examination of eligibility for insurance. On the other hand, in the case of the red rank or the yellow rank, since there is a possibility that the subject has cancer, it is recommended to perform determination again by the determination method of the present invention or to perform a careful inspection by another method.

Note that the above procedure is an example, and can be arbitrarily changed. For example, in the present embodiment, the reference amount is measured before the dropping of the specimen, but the reference amount may be measured immediately after the dropping of the specimen. Here, "immediately after the dropping of the specimen" indicates after the lapse of such a short time that the attracting behavior or the repelling behavior of the nematodes does not occur after the dropping of the specimen. As described above, if the measured value is a measured value before the attracting behavior or the repelling behavior of the nematodes occurs, there is no problem even when the measured value is used as a comparison target with respect to the determination amount after the movement, so that the measured value can be similarly used as the reference amount.

In addition, for example, in steps S6 to S10, it is sufficient that stages can be divided into three stages of red, blue, and yellow on the basis of the value calculated in step S5, and the upper limit value and the lower limit value, and the order of comparison may be changed. That is, for example, the order of step S6 and step S8 may be changed.

In addition, each process excluding step S2 may be executed by a computer. Specifically, for example, it is assumed that a microcomputer, a storage device, and the like are provided in a measurement unit of a measurement device to be described later, step S4 is executed after a predetermined time from step S1, and the computer executes the calculations of steps S5 to S10.

Next, a container, a measurement device, and a floor plate used in the present embodiment will be described with reference to FIGS. 2 to 15.

Figure 2:
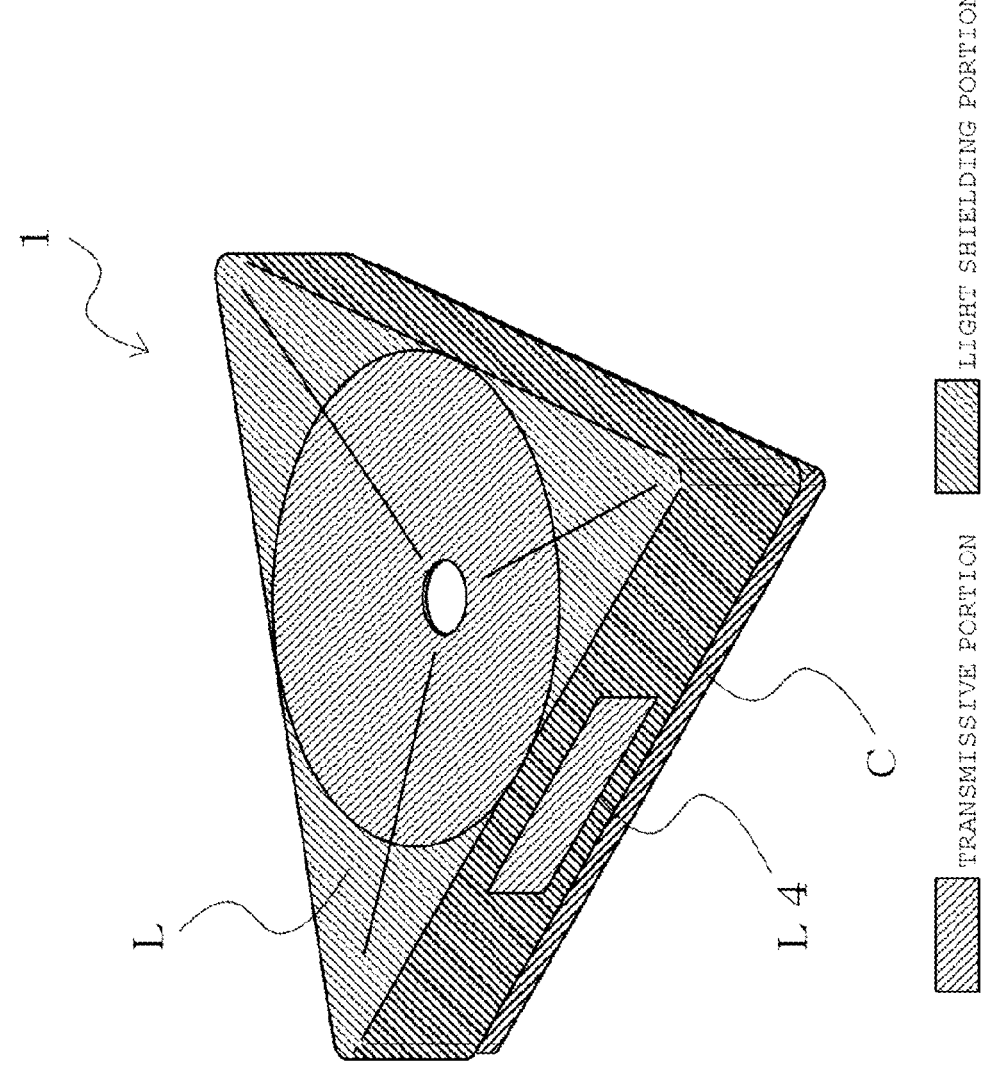
FIG. 2 is a schematic perspective view of a petri dish used in the embodiment of the present invention.

FIGS. 2 to 7 are views illustrating a structure of a petri dish used as the container in the present embodiment. As illustrated in FIG. 2, a petri dish 1 includes a container main body C and a lid body L that covers the container main body C.

Figure 3:
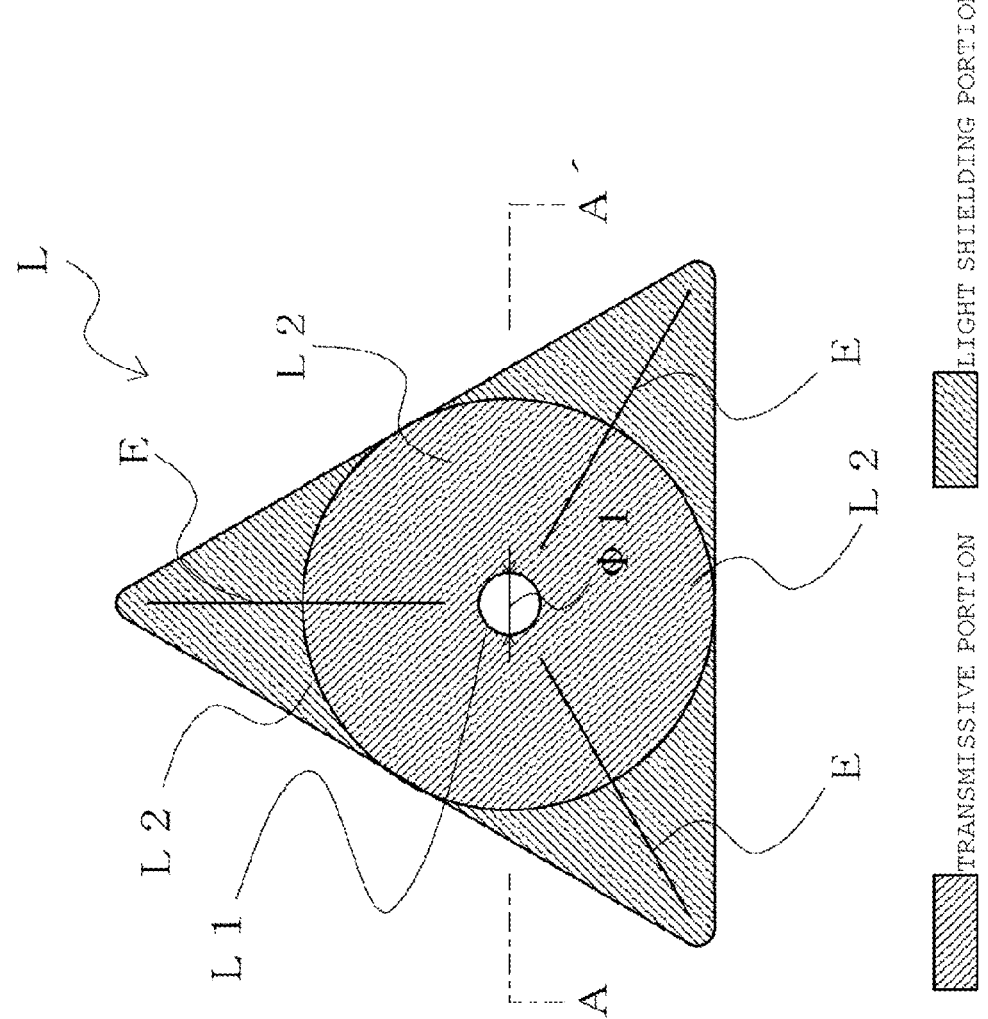
FIG. 3 is a plan view of a lid body in the petri dish used in the embodiment of the present invention.

As illustrated in FIG. 3, the lid body L has a substantially triangular shape in plan view, and has one through hole L1 communicating the container main body C with an external space and three inclined surfaces L2 on a top surface thereof. In addition, in order to be able to measure the illuminance (amount related to light) in a state where the lid body L is mounted, it is preferable that at least a portion of the lid body L that is in contact with immediately above the measurement range is made of a material that transmits light. In the present embodiment, the lid body L includes a transmissive portion formed in a shape substantially equidistant from the through hole L1.

More specifically, the through hole L1 is formed substantially at the center of the top surface. Each of the inclined surfaces L2 is defined by a ridge E extending from each corner portion of the top surface toward the through hole L1 so as to have a substantially uniform area, and is formed so as to be gradually inclined downward toward the through hole L1. In the present embodiment, a diameter $\Phi 1$ of the through hole L1 is configured to be about 9 mm. Here, if a transmissive portion made of a material that transmits light is provided only around the through hole L1, and the other portions are shielded from light, it is possible to reliably set the periphery of the through hole L1, which is the dropping position of the specimen, as a measurement range.

Figure 4:
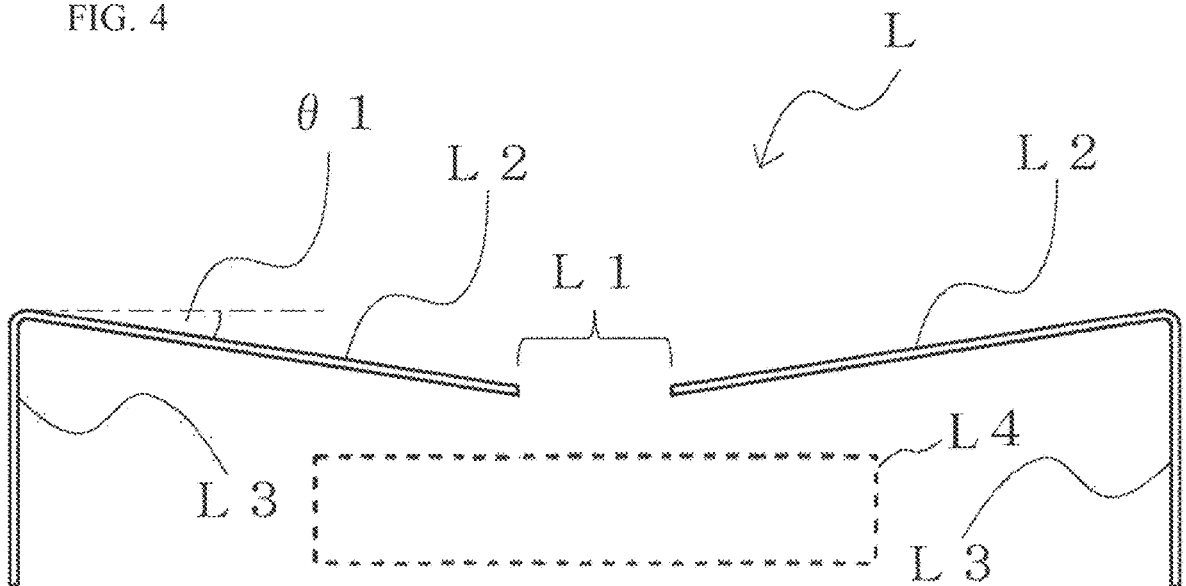
FIG. 4 is an enlarged view of an end face of an A-A' line cut portion of the lid body in the petri dish used in the embodiment of the present invention.

As illustrated in FIG. 4, the lid body L has a side wall portion L3 extending downward from a peripheral edge of the top surface.

Although an inclination angle $\theta 1$ of each inclined surface L2 is about 10 degrees, the inclined surface may be inclined at an inclination angle larger than the inclination angle $\theta 1$ in order to increase the arrival speed of the dropped liquid to the through hole L1.

Here, although the side wall portion L3 is shielded from light, the side wall portion includes a transmissive portion L4 that transmits light. As a result, the light emitted from the side surface is transmitted into the petri dish. The transmissive portion L4 may be made of a material that transmits light of an illuminator in a measurement device to be described later, or may be a window that penetrates an internal space and an external space of the lid body L. Here, an example in which the transmissive portion L4 is provided only in one side wall portion L3 is illustrated, but a plurality of transmissive portions L4 may be provided.

Figure 5:
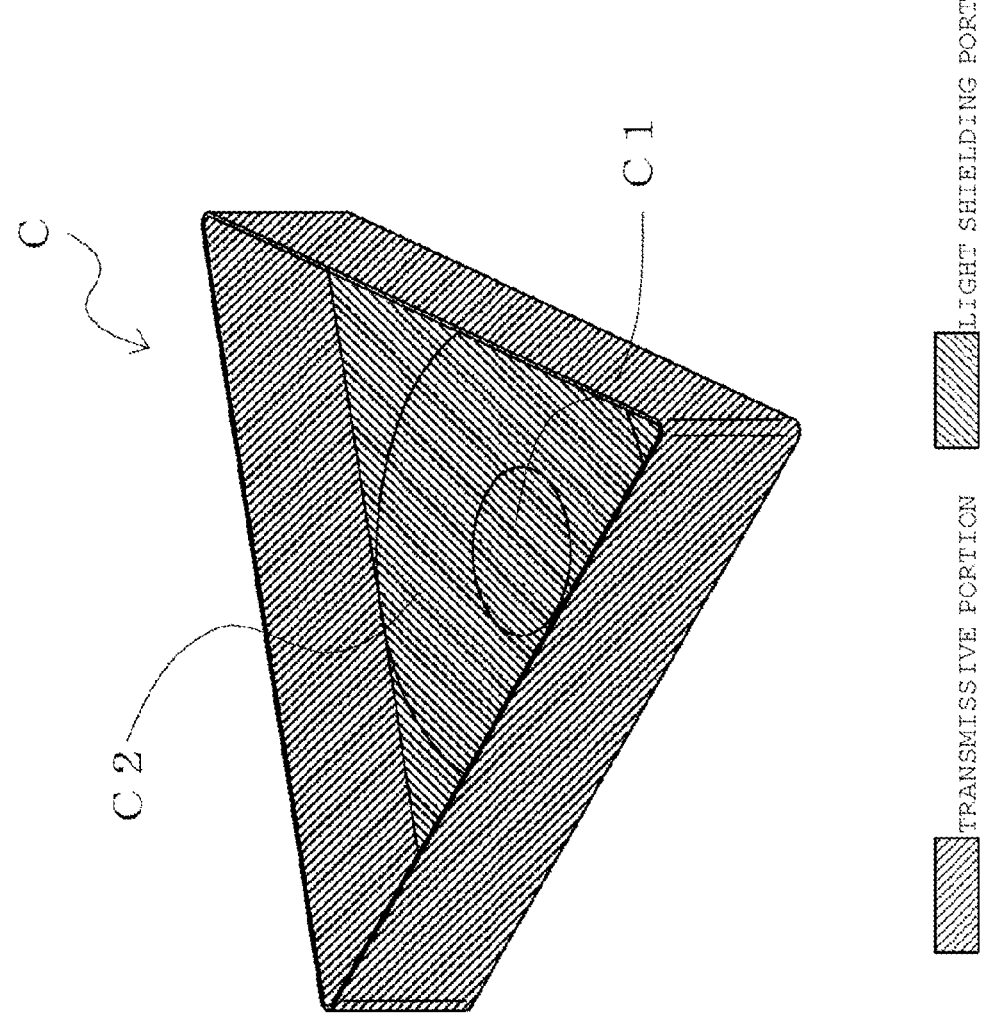
FIG. 5 is a schematic perspective view of a container main body in the petri dish used in the embodiment of the present invention.
Figure 6:
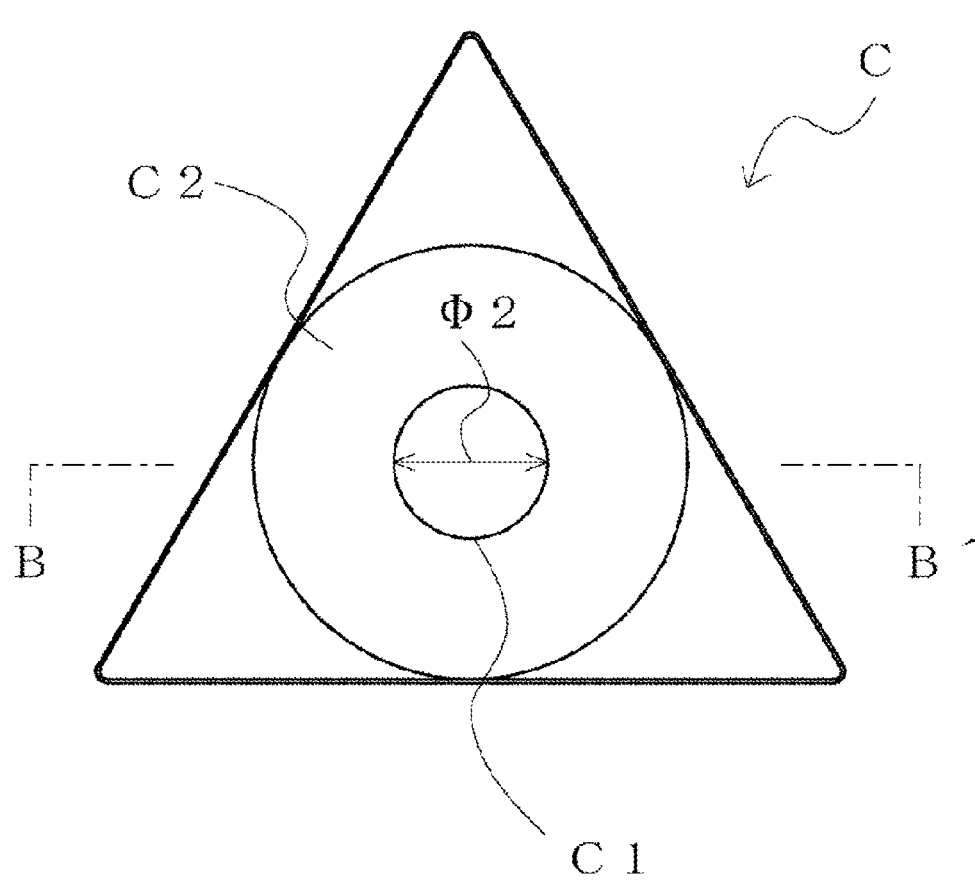
FIG. 6 is a plan view of the container main body in the petri dish used in the embodiment of the present invention.

As illustrated in FIGS. 5 and 6, the container main body C has a substantially triangular shape in plan view, and has a liquid reservoir portion C1 and an inclined surface C2 on a bottom surface thereof.

More specifically, the liquid reservoir portion C1 has a circular shape in plan view, and is formed substantially at the center of the bottom surface so as to be substantially coaxial with the through hole L1 at the time of being covered with the lid body L. The inclined surface C2 has a circular shape inscribed in the bottom surface in plan view, and is formed so as to be gradually inclined downward toward the liquid reservoir portion C1.

In the present embodiment, a diameter @2 of the liquid reservoir portion C1 is configured to be about 20 mm.

Figure 7:
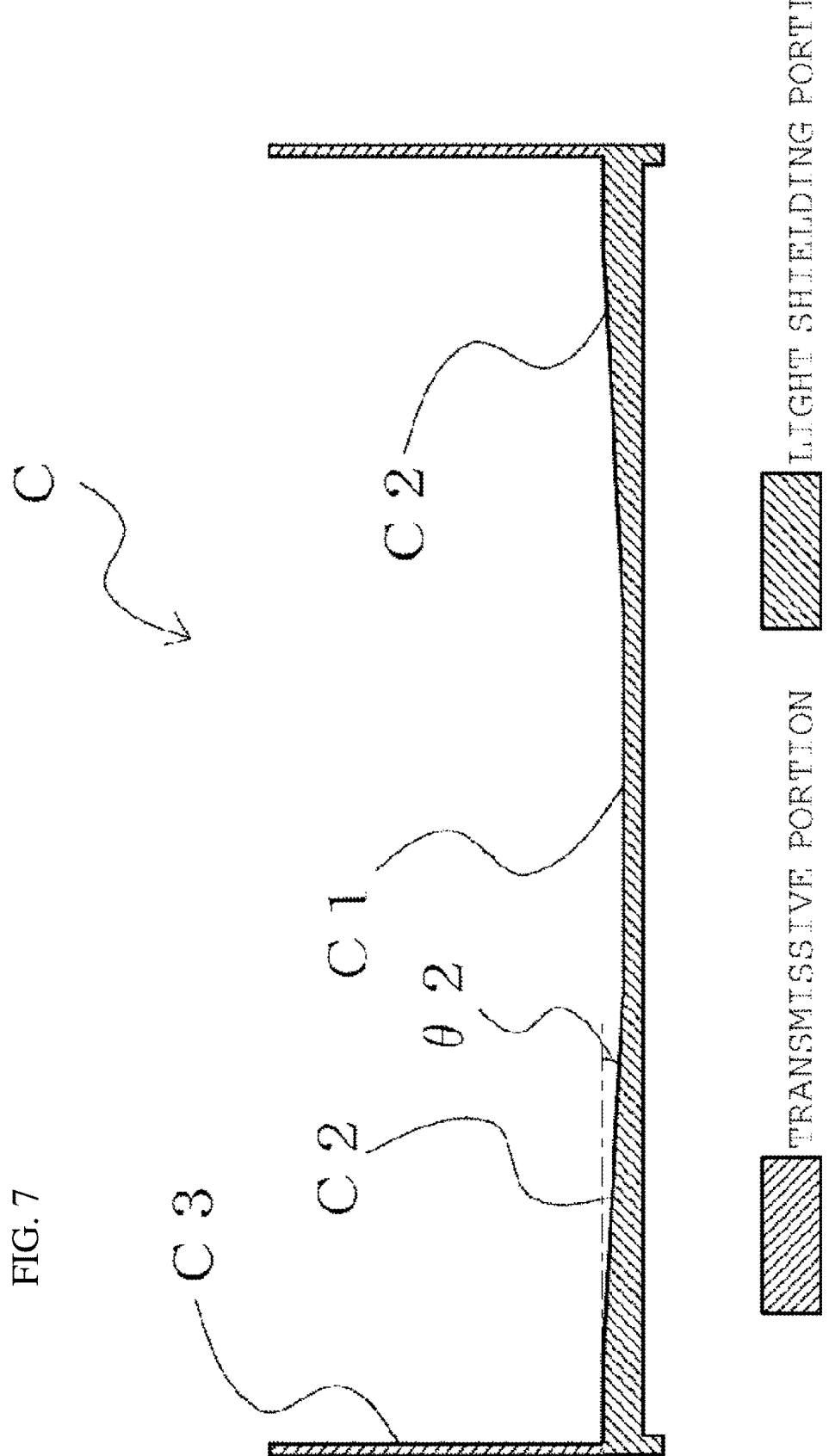
FIG. 7 is an enlarged view of an end face of a B-B' line cut portion of the container main body in the petri dish used in the embodiment of the present invention.

As illustrated in FIG. 7, the container main body C has a side wall portion C3 extending upward from a peripheral edge of the bottom surface. The side wall portion C3 transmits light at least at a position corresponding to the transmissive portion L4 when the lid body L is attached. In the present embodiment, the entire side wall portion C3 transmits light. The lid body L is attached to the container main body C such that an inner peripheral surface of the side wall portion L3 abuts on an outer peripheral surface of the side wall portion C3. Here, the side wall portion L3 of the lid body L covers the side wall portion C3 of the container main body, so that light outside the petri dish 1 is shielded on the side surface excluding the transmissive portion L4.

Although the inclination angle $\theta 2$ of the inclined surface C2 is about 5 degrees, the inclined surface may be inclined at an inclination angle larger than the inclination angle $\theta 2$ in a case where it is desired to increase the burden when the nematodes climb the inclination and to more clearly visually recognize the strength of the repelling behavior against the odor.

Here, the bottom surface of the container main body C including the liquid reservoir portion C1 and the inclined surface C2 is used in a state where the nematodes are freely movable. For example, it is assumed that a medium having a uniform thickness is provided, or the bottom surface is constituted by a material where the nematodes can move. The bottom surface of the container main body C is preferably shielded from light.

In the present embodiment, the lid body L and the container main body C have substantially triangular shapes in plan view, but the shapes thereof are not limited. For example, the shape may be another polygonal shape or a circular shape in plan view.

Figure 8:
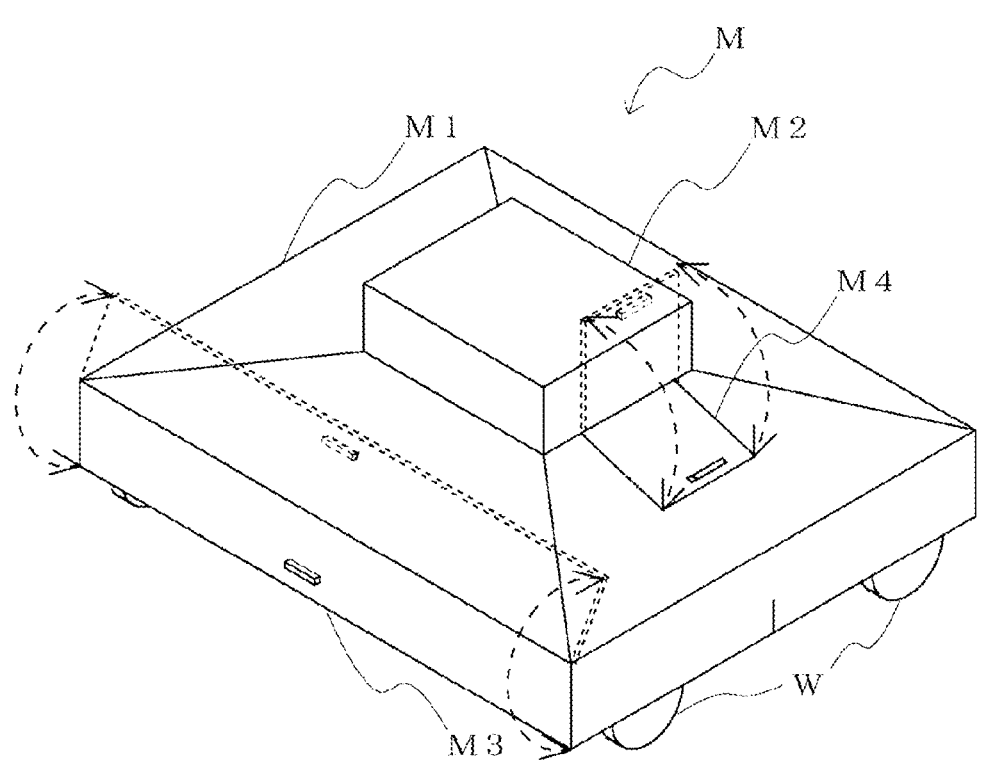
FIG. 8 is a schematic perspective view of a measurement device used in the embodiment of the present invention.

FIGS. 8 to 12 are views illustrating a structure of a measurement device used in the present embodiment. As illustrated in FIG. 8, a measurement device M includes a main body portion M1 and a measurement unit M2. The measurement unit M2 is provided at upper part of the main body portion M1. Further, a wheel W is provided below the main body portion M1, and the measurement device M can move in a certain direction. The main body portion M1 is preferably made of a light shielding material so that external light does not affect illuminance measurement. In the present embodiment, the measurement device M shields the external light, but the present invention is not limited thereto. For example, measurement under the same conditions may be realized by light shielding and transmissive functions of the petri dish 1, and only light irradiation and measurement may be performed in the measurement device M.

An input port M4 is further provided on the main body portion M1, and the specimen can be dropped on the petri dish 1 inside the main body portion M1 by opening a door, and the illuminance measurement under the same condition can be performed by closing the door at the time of measuring the illuminance.

A container introduction port M3 for taking in and out the container is provided on a side surface of the main body portion M1 in a direction substantially perpendicular to a traveling direction of the wheel, and when a light shielding material is used as a material of the door, it is possible to take in and out the container and to switch shielding of external light by opening and closing the door.

Figure 9:
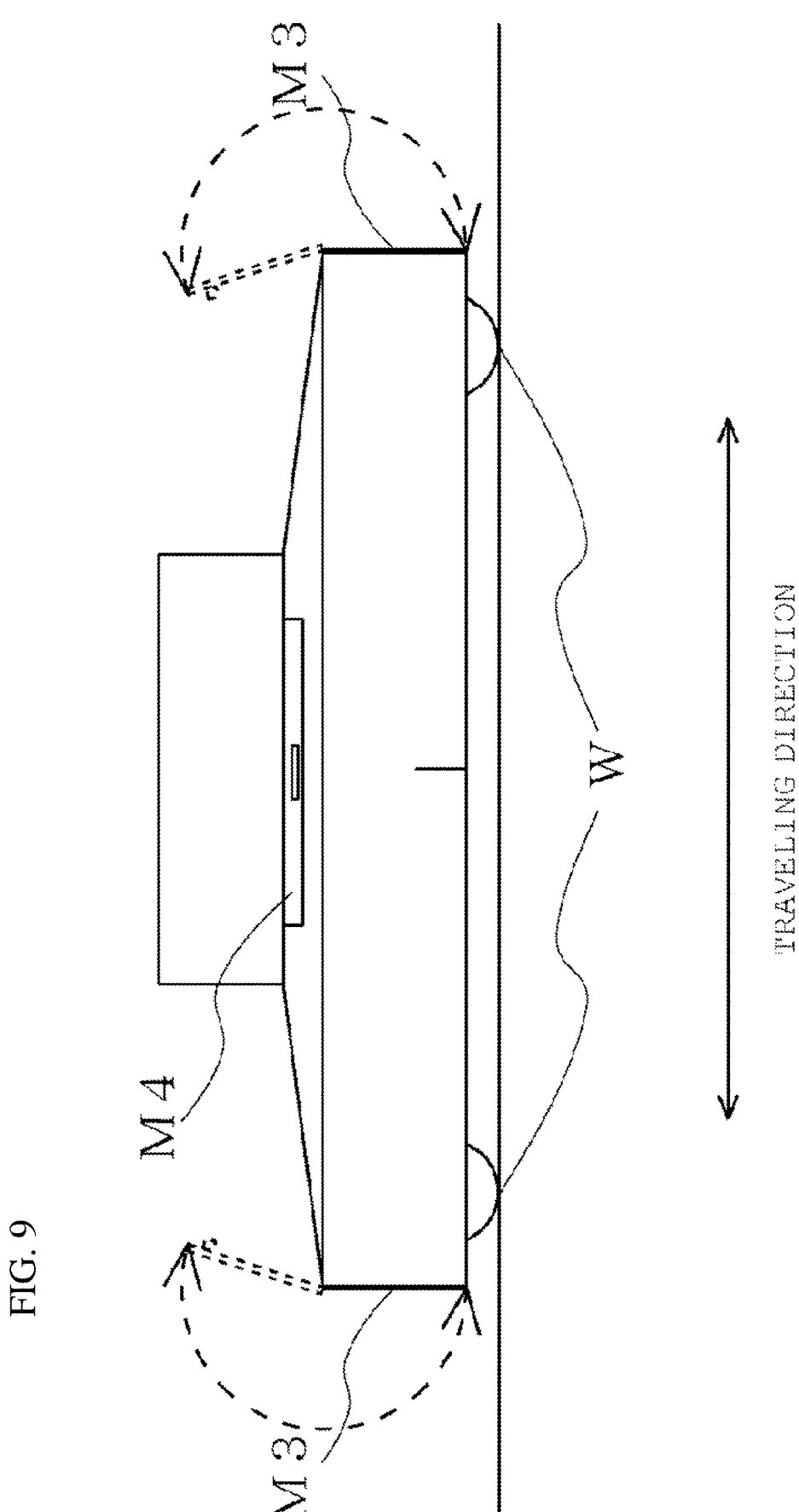
FIG. 9 is a schematic side view of the measurement device used in the embodiment of the present invention.

As illustrated in FIG. 9, in the present embodiment, the container introduction port M3 is provided on two side surfaces in a direction substantially perpendicular to the traveling direction of the wheel W, and is configured to penetrate the main body portion M1 in a direction along the traveling direction of the wheel W when both doors are opened. As a result, the petri dish 1 is arranged along the traveling direction of the wheel W, the door of the container introduction port M3 is opened and the measurement device M is moved onto the petri dish 1, and after the movement, the door of the container introduction port M3 is closed and the measurement is performed. Therefore, the illuminance (the reference amount and the determination amount) can be continuously and efficiently measured and determined using a plurality of petri dishes 1.

Figure 10:
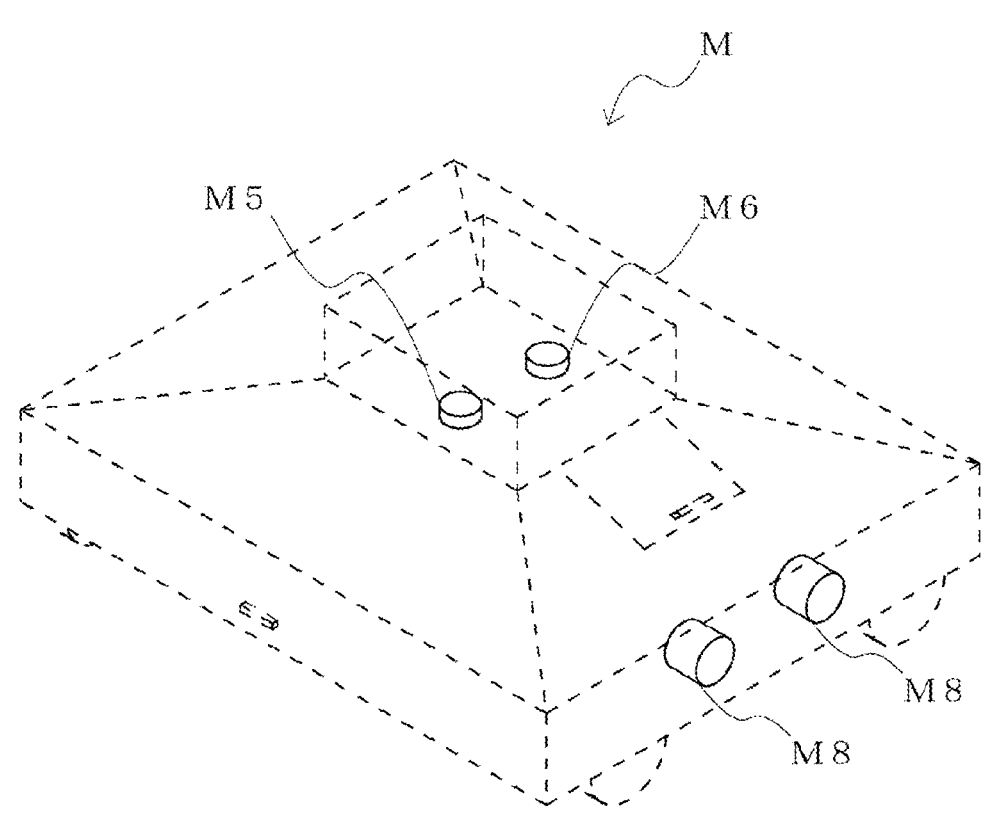
FIG. 10 is a perspective view illustrating positions of an illuminator and a measurement unit in the measurement device used in the embodiment of the present invention.

As illustrated in FIG. 10, the measurement unit M2 provided on the main body portion M1 of the measurement device M includes an illuminometer M5 and an imaging unit M6. The illuminometer M5 measures the illuminance in the measurement range from above the petri dish 1 as the amount related to light. The imaging unit M6 captures an image of the petri dish 1 from above for recording. For example, by recording a serial number or the like on the lid body L of the petri dish 1 and photographing the serial number or the like, association between a determination result and an individual becomes easy.

Here, the measurement range is preferably set as a predetermined range around the specimen dropping position in the petri dish. For example, it is preferable to set a range that includes the liquid reservoir portion C1, is wider than the liquid reservoir portion C1, and does not include the entire petri dish 1 or the outside of the petri dish as the measurement range. When the measurement is performed by moving the measurement device M as in the present embodiment, it is difficult to fix a positional relation between the measurement device M and the petri dish 1. However, by determining the behavior of the nematodes by comparing the reference amount and the determination amount measured in the same positional relation, illumination condition, and measurement range, it is possible to suppress an influence on the determination result to be small without accurate fixing at the same position.

Figure 11:
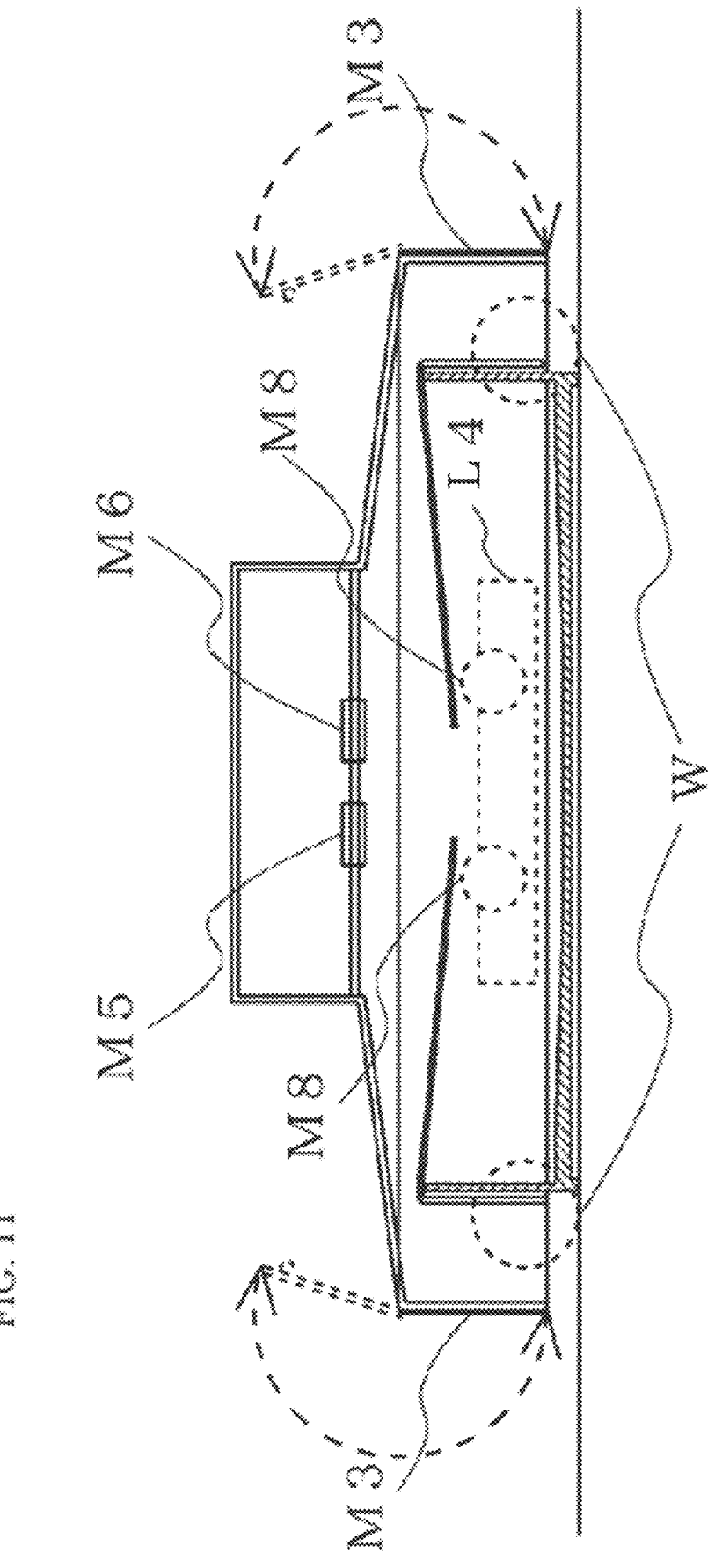
FIG. 11 is a cross-sectional view of a side surface direction cut portion of the measurement device used in the embodiment of the present invention.

As illustrated in FIG. 11, at the time of measurement, the petri dish 1 is covered with the main body portion M1 of the measurement device M, and an illuminator M8 irradiates the inside of the petri dish 1 with light through the transmissive portion L4. Here, the illuminator M8 may emit light of a specific wavelength including visible light and invisible light. In this case, the illuminometer M5 measures the illuminance of the light of the specific wavelength. As the light of the specific wavelength, it is preferable to select a wavelength that does not affect the activity of the nematodes. The wheel W is provided at a position that does not block the light emitted by the illuminator M8.

Figure 12:
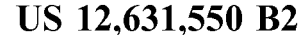
FIG. 12 is a cross-sectional view of a front direction cut portion of the measurement device used in the embodiment of the present invention.
Figure 13:
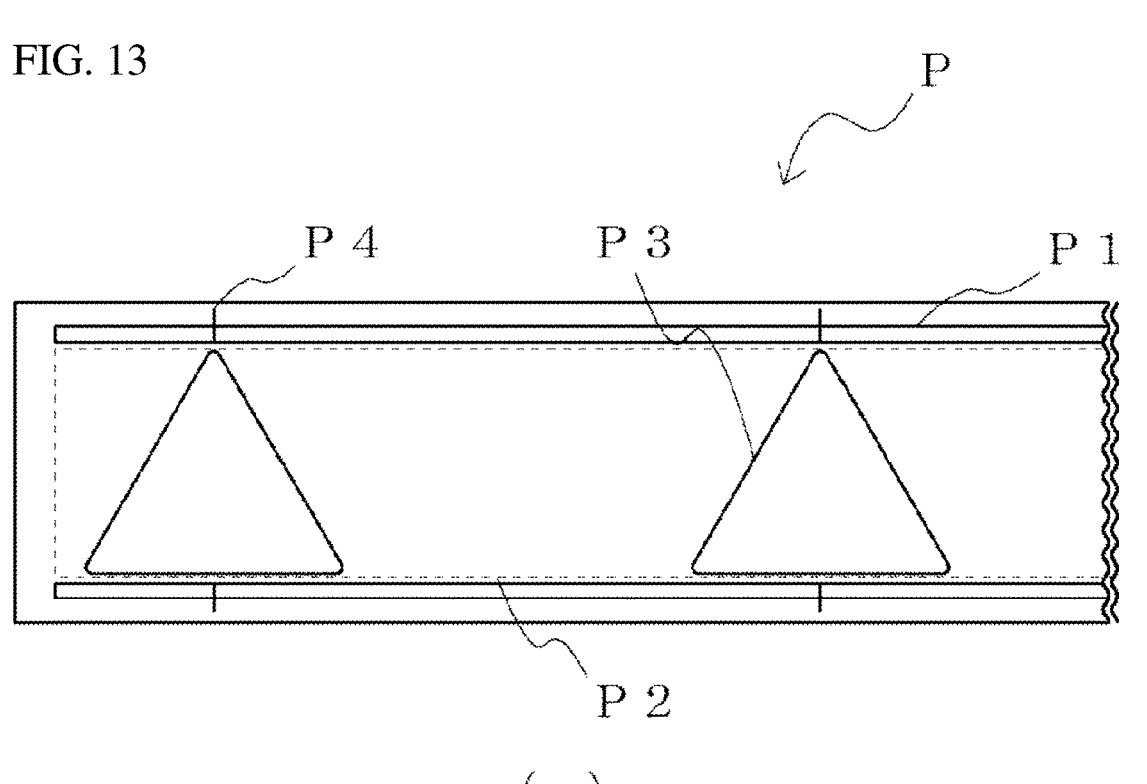
FIG. 13 is a plan view of a floor plate used in the embodiment of the present invention.
Figure 13:
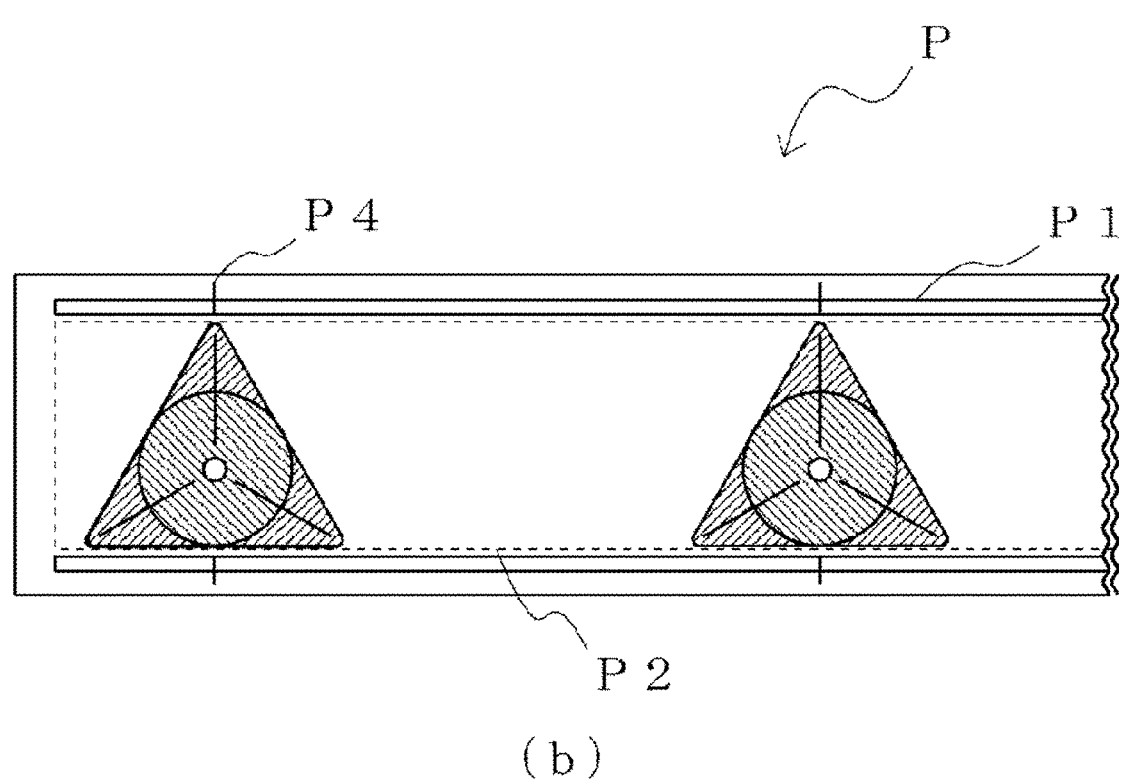

As illustrated in FIG. 12, at the time of measurement, the input port M4 is located immediately above the petri dish 1, and the door is opened to drop the specimen from the input port M4, so that the dropped specimen travels along the inclined surface L2 of the lid body L by gravity and is reliably accommodated in the container main body C through the through hole L1.

FIG. 13(a) is a plan view of a floor plate P used in the present embodiment. As illustrated in FIG. 13(a), the floor plate P of the present embodiment includes a boundary portion P1, a container placement portion P2 defined by the boundary portion P1, a container position P3 serving as a guide of a position where the container is placed, and an auxiliary line P4 serving as a guide of a stop position of the measurement device M.

In the present embodiment, the outline of the container (petri dish 1) is displayed as the container position P3, but the format is not limited as long as it serves as a guide for placing the container. For example, a part of the outline of the container may be displayed, or a recess in the shape of the container shallower than a lower end of the transmissive portion L4 may be provided as the container position P3, and the container may be installed in the recess.

Further, the boundary portion P1 may also be expressed in an arbitrary format. For example, the boundary portion P1 is expressed as a convex portion, and the wheel W travels outside the convex portion, so that the traveling position is less likely to deviate. In addition, by providing a groove as the boundary portion P1 and causing the wheel W to travel in the groove, it is easy to cause the wheel to travel at an intended position.

FIG. 13(b) illustrates an installation example of the petri dish 1 on the floor plate P. In this manner, the petri dish 1 is disposed according to the container position P3 so as to have a sufficient interval.

Figure 14:
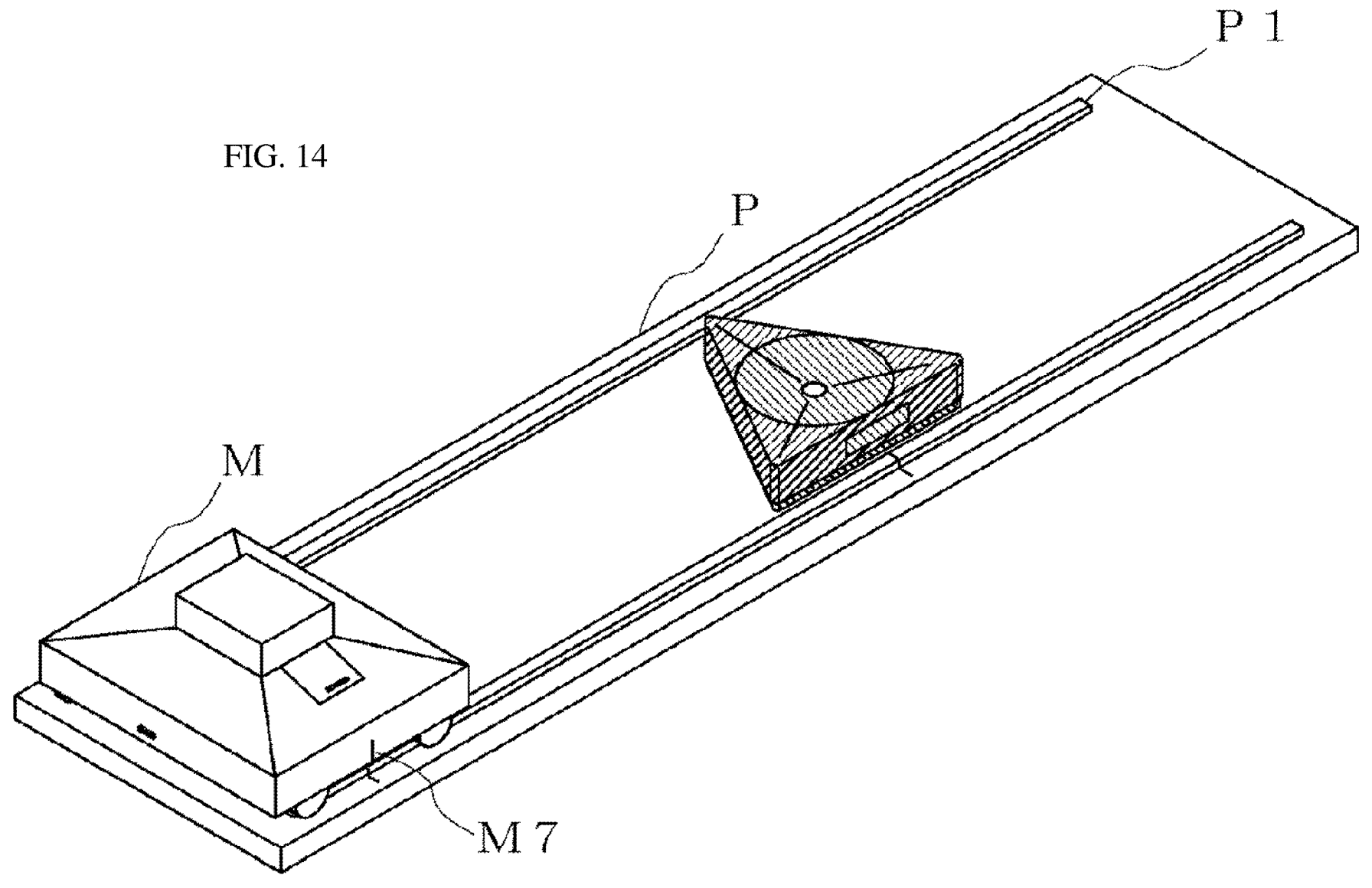
Figure 15:
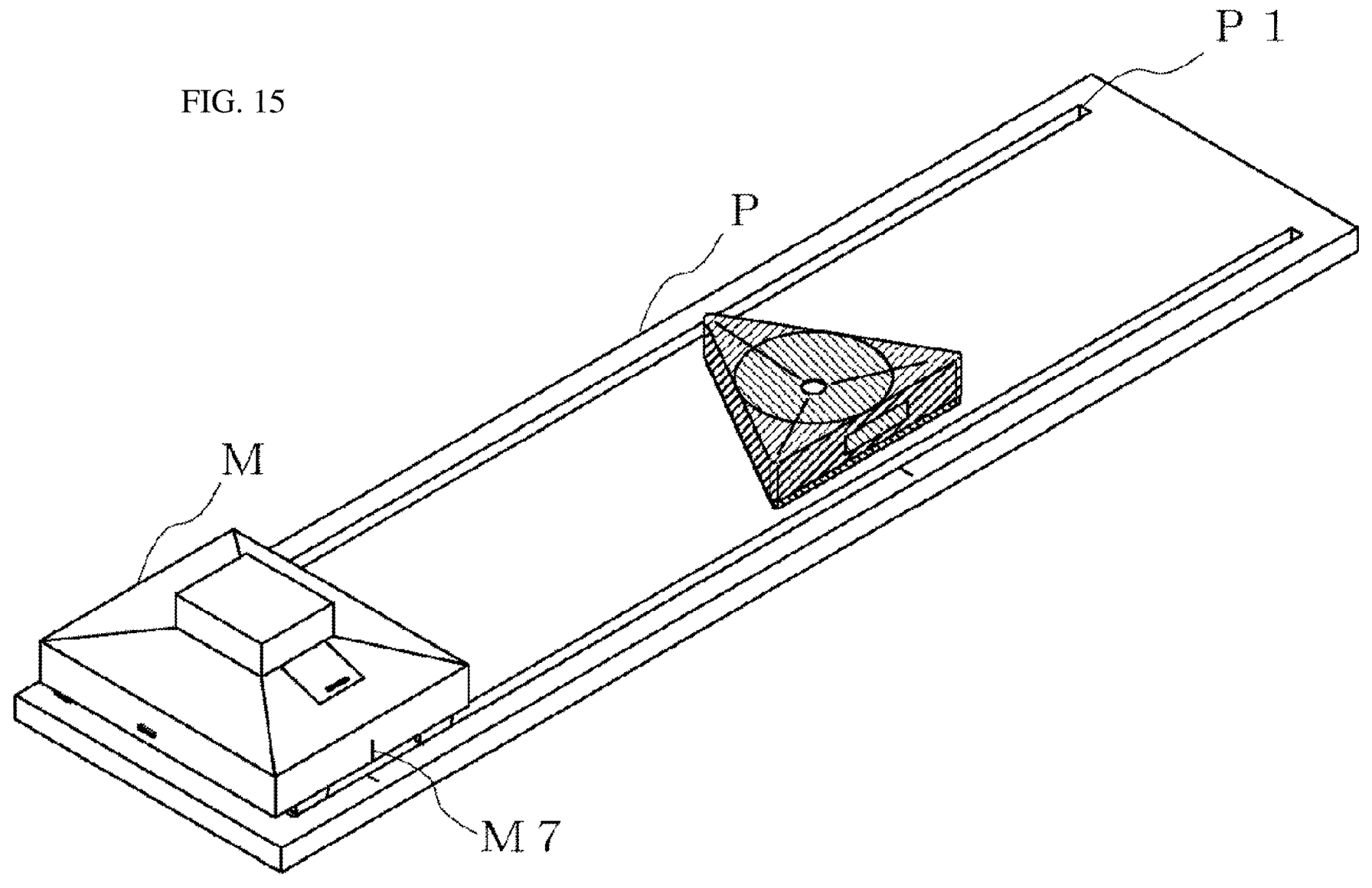

At the time of measurement, as illustrated in FIGS. 14 and 15, the petri dish 1, the measurement device M, and the floor plate P are used. FIG. 14 illustrates an example of a case where a convex portion is provided as the boundary portion P1. FIG. 15 illustrates an example of a case where a groove is provided as the boundary portion P1.

The measurement device M of the present embodiment includes an auxiliary line M7 on the side surface. By matching position of the auxiliary line M7 of the measurement device M and the auxiliary line P4 of the floor plate P at the time of measurement, the petri dish 1 and the measurement device M have an appropriate positional relation as illustrated in FIGS. 11 and 12.

In addition, the measurement device M may be easily stopped at an appropriate position by providing a mark, a recess, or the like at a stop position of the wheel W corresponding to the container position P3 on the traveling position of the wheel W.

As described above, according to the present embodiment, it is possible to easily and efficiently determine the behavior of the nematodes. In particular, by using the measurement device M described above, the reference amount and the determination amount can be measured under the same condition, and determination can be performed with higher accuracy. In addition, since the measurement device M includes the wheel, measurement can be continuously performed for a plurality of containers, and efficiency is further improved.

REFERENCE SIGNS LIST

1 Petri dish
L Lid body
L1 Through hole
L2 Inclined surface

L3 Side wall portion
L4 Transmissive portion
E Ridge
C Container main body
C1 Liquid reservoir portion
C2 Inclined surface
C3 Side wall portion
M Measurement device
M1 Main body portion
M2 Measurement unit
M3 Container introduction port
M4 Input port
M5 Illuminometer
M6 Imaging unit
M7 Auxiliary line
M8 Illuminator
W Wheel
P Floor plate
P1 Boundary portion
P2 Container placement portion
P3 Container position
P4 Auxiliary line

The invention claimed is:

1. A measurement device comprising:

a main body portion that is provided with an input port to drop a liquid containing a biological substance into a container in which a nematode is movably stored, and that covers the container after the liquid is dropped into the container;

an illuminator that is provided inside a side surface of the main body portion and that emits light on a side surface of the container for measurement:

as a reference amount, a photometric quantity in a measurement range narrower than the container including a place in which the dropped liquid exists and a vicinity thereof in the container irradiated with light by the illuminator before or immediately after the dropping of the liquid, and as a determination amount, a photometric quantity in the measurement range in the container irradiated with light after an observation time provided for movement of the nematode elapses from the dropping of the liquid; and an illuminometer and an imaging unit that are provided at an upper part of the main body portion and that measure the photometric quantity from above the container to determine whether or not the determination amount has decreased by comparison with the reference amount.

2. The measurement device according to claim 1, further comprising:

a computer that determines that the subject is eligible for insurance as a healthy person when it is considered that the determination amount has decreased, and gives a notification for prompting an inspection when it is considered that the determination amount has increased or when it is considered that there is no change in the determination amount.

3. The measurement device according to claim 2, wherein the computer further:

considers that the determination amount has decreased when a difference obtained by subtracting the reference amount from the determination amount or a ratio obtained by dividing the determination amount by the reference amount is less than a lower limit value, considers that the determination amount has increased when the difference obtained by subtracting the reference amount from the determination amount or the ratio obtained by dividing the determination amount by the reference amount exceeds an upper limit value, and considers that there is no change in the determination amount when the difference obtained by subtracting the reference amount from the determination amount or the ratio obtained by dividing the determination amount by the reference amount is between the upper limit value and the lower limit value.

4. The measurement device according to claim 1, wherein the main body portion includes the input port at a position higher than a height of the container.

5. The measurement device according to claim 1, further comprising:

a wheel, wherein the reference amount and the determination amount are continuously measured for a plurality of containers by the illuminometer and the imaging unit being moved by the wheel.

6. The measurement device according to claim 5, wherein the main body portion includes a container introduction port for taking in and out the container on a side surface in a direction substantially perpendicular to a traveling direction of the wheel.

7. A measurement system comprising:

the measurement device according to claim 5; and a floor plate, comprising:

a container placement portion on which the container is placed, and a boundary portion that defines a boundary between an inner side and an outer side of the container placement portion, wherein the wheel travels outside the container placement portion.

* * * * *